United States Patent [19]

Dietlin et al.

[11] Patent Number: 5,219,552
[45] Date of Patent: Jun. 15, 1993

[54] COMPOSITIONS INTENDED FOR USE IN TOMO DENSITOMETRY

[76] Inventors: François Dietlin, 17 Rue du Maréchal Foch, 78110 Le Vesinet; Fernand Heitz, 3 Avenue des Marroniers, 94120 Fontenay S/Bois, both of France

[21] Appl. No.: 139,250
[22] PCT Filed: Apr. 7, 1986
[86] PCT No.: PCT/FR86/00116
§ 371 Date: Jan. 4, 1988
§ 102(e) Date: Jan. 4, 1988
[87] PCT Pub. No.: WO87/06139
PCT Pub. Date: Oct. 22, 1987
[51] Int. Cl.5 .................. A61K 49/04; A61K 49/00
[52] U.S. Cl. .............................. 424/4; 424/9
[58] Field of Search ......................... 424/9, 4
[56] References Cited

U.S. PATENT DOCUMENTS

| | | | |
|---|---|---|---|
| 3,542,915 | 11/1970 | Bodkin | 424/4 |
| 3,832,457 | 8/1974 | Sugimoto et al. | 424/4 |
| 4,423,158 | 12/1983 | Porath | 521/32 |
| 4,647,447 | 3/1987 | Gries et al. | 424/9 |
| 4,885,363 | 12/1989 | Tweedle et al. | 540/465 |

FOREIGN PATENT DOCUMENTS 0173629 5/1986 European Pat. Off.
3401052 7/1984 Fed. Rep. of Germany.

OTHER PUBLICATIONS

Skucas, Jovitas "Agents in computed Tomography", *Radiographic Contrast Agents*, pp. 109–116.

Primary Examiner—Frederick E. Waddell
Assistant Examiner—K. Weddington
Attorney, Agent, or Firm—Bierman and Muserlian

[57] ABSTRACT

The present invention relates to measurements by tomo-densitometry. It relates in particular to compositions usable in tomo-densitometry which are comprised of a solution consisting at least of a salt or a complex of a metal of which the atomic weight is comprised between 24 and 66 associated with an appropriate solvent or vehicle. Utilization in tomo-densitometry.

9 Claims, No Drawings

COMPOSITIONS INTENDED FOR USE IN TOMO DENSITOMETRY

The method of X-ray tomo-densitometry is an exploring and imaging process of the human body which allows inter alia the evidencing of full organs.

The study of the abdominal organs in X-ray tomo-densitometry needs the use of contrast agents for a better identification of the anatomical features.

So through the endovenous injection of water-soluble iodinated compounds called Angio-scan, it has been possible to evidence the vessels as well as the parenchym of full organs (liver, spleen..).

The hollow organs are difficult to investigate in spite of the use of very diluted iodinated compounds given by oral way. Their optical density on one hand and their lack of homogeneity on the other hand is why they failed to respond to the hopes expressed for the anatomical indentification and diagnosis of pathological elements.

The utilization of new constrast agents based on concentrated solutions of metals such as calcium, magnesium or zinc reply to the above-cited criticisms:

They fill the entirety of the lumen of digestive tract in less than one hour without leaving an anatomical empty space.

They underline in a perfect manner the walls of the digestive tract.

Their optical density is such that they cannot be mistaken with an anatomical or anatomopathological element in the vicinity.

They can also be used for the showing of the bladder and the urogenital tract.

The compositions according to this invention are solutions in water or in an aqueous medium compatible with the body fluids, containing at least a salt of a metal having an atomic weight comprised between 24 and 66 or a complex of Cobalt or Zinc with a chelating agent.

Among the above-defined metals they may be more particularly be cited derivatives of Magnesium, derivatives of Calcium, derivatives of Manganese, derivatives of Iron, derivatives of Zinc and derivatives of Cobalt.

The salts which are used are those soluble in water and allowing to realize concentrated solutions having from 5 to 25% of the metallic derivative.

To this end, it will be preferably used, a chloride, a nitrate, sulphate, an acetate, and especially a metallic gluconate, lactobionate, glucoheptonate or glucono-glucoheptonate.

So it will be advantageous to use a solution of magnesium chloride, of calcium nitrate, of ferrous gluconate, of calcium lactobionate, of calcium gluconoglucoheptonate, of zinc sulphate, of manganese actate, or of magnesium formate.

It may also be advantageous in the case of Cobalt or Zinc derivatives, to use them in the form of complexes soluble in water such as those of Ethylenediaminotetracetic acid, those of Ethyleneglycol bis ( -aminoethylether) N,N, N',N'-tetracetic acid, those of ethylenediamine NN-diacetic N',N'-di-propionic acid or those of ethylene diamine NN-diacetic N'N'-di- propionic acid. These complexes may more precisely be constituted of mixed molecules containing from two to four alkali metal ions as for example the complexe of ethylenediamine tetracetic acid with zinc in the form of tetra sodium salt.

The use of these complexes, includes the advantage of having a limited taste, and a lack of toxicity.

The solutions according to this invention may also be admixed with a thickening agent, an agent which increases the viscosity, a sweetening agent, a flavouring agent.

The solutions are intended to be given orally in the form of a solute, a syrup or a potion; rectally as an enema or by endocavitar way as for example by instillation in the bladder or the urogenital tract.

In a preferred manner one utilizes an aqueous solution containing 5, 10 or 15% of a salt of a metal the atomic weight of which is comprised between 24 and 66, sweetened with a synthetic sweetening agent such as Aspartame or a saccharinate as for example the to sodium or the calcium derivative.

They may also be utilized mixed solutions which contain a mixture of the above cited metallic derivatives in a respective ratio ranging from 1 to 99% as for example a solution containing equal parts of a magnesium salt and a calcium salt. These salts may be derived from the same anion or, except for chemical unsuitability, from two different anions.

For examination of the organs and namely those of the digestive tract, the compositions according to this invention may moreover include a drug which modifies the motility, and preferably a drug which decreases or suppress the intestinal peristaltism. There may be cited in this respect, trimebutine and its addition salts, the salts of N-methyl scopolamine, the salts of N-butylhyoscine, the addition salts of Prifinium, the addition salts of Difemerine, the addition salts of Atropine, the addition salts of hyosciamine, the addition salts of scopolamine, the addition salts of pentapriperium, mepenzolate hydrobromide, piperidolate hydrochloride, pinaverium hydrobromide, mebeverine hydrochloride, octaverine hydrochloride or oxyphencyclimine hydrochloride.

The volume of solution which has to be given, may vary from 50 to 500 ml and preferably from 100 to 300 ml depending on the way of administration.

The solutions according to this invention thus allow examinations of the digestive tract (upper part or lower part), of the bladder and of the jurogenital tract by X-ray tomodensitometry more fine, more contrasted and insuring to better appreciate the outlines of hollow organs.

The following examples illustrate the invention. They do not limit it in any manner:

EXAMPLE I

Solution of calcium gluconate

| | |
|---|---|
| Calcium gluconate | 25 g |
| cross linked carboxymethy cellulose | 0.25 g |
| Aspartame | 0.05 g |
| flavour coffee | enough for |
| distilled water | enough for 250 ml |

EXAMPLE II

Solution of calcium glucono-glucoheptonate

| | |
|---|---|
| calcium gluco-glucoheptonate | 30 g |
| glycerol | 5 g |
| Aspartame | 0.05 g |
| Flavour coffee | enough for |

| distilled water | enough for 200 ml |
|---|---|

EXAMPLE III

Solution of ferrous gluconate

| ferrous gluconate | 30 g |
|---|---|
| hydroxypropylmethylcellulose | 0.10 g |
| sodium saccharinate | 0.15 g |
| distilled water | enough for 200 ml |

EXAMPLE IV

Solution of Magnesium acetate

| Magnesium acetate as the tetrahydrate | 37 g |
|---|---|
| Glycerol | 13 g |
| sodium saccharinate | 0.15 g |
| distilled water | enough for 200 ml |

EXAMPLE V

Solution of magnesium gluconate

| magnesium gluconate (as the hemi magnesium salt) | 46 g |
|---|---|
| methylcellulose | 4 g |
| glycerol | 10 g |
| Aspartame | 0.05 g |
| distilled water | enough for 200 ml |

EXAMPLE VI

Solution of calcium lactobionate

| calcium lactobronate (as the hemi-calcium salt) | 27.5 g |
|---|---|
| magnesium acetate | 14 g |
| distilled water | enough for 200 ml |

EXAMPLE VII

Solution of cobalt

| disodium cobalto ethylene diaminotetra acetate | 65 g |
|---|---|
| carboxymethylcellulose | 2.5 g |
| glycerol | 12 g |
| distilled water | enough for 250 ml |

EXAMPLE VIII

Solution of calcium gluconate

| calcium gluconate | 25 g |
|---|---|
| cross linked carboxymethylcellulose (as the sodium salt) | 0.05 g |
| Prifinium bromide | 0.05 g |
| calcium saccharinate | 0.15 g |
| distilled water | enough for 200 ml |

What is claimed is:

1. In the method of X-ray tomodensitometry of a warm-blooded animal, the improvement comprising using as the contrasting agent an aqueous solution containing an X-ray tomodensitometrically effective amount of at least a water-soluble salt or complex of a metal with an atomic weight between 24 and 66, dispersed in an aqueous medium.

2. The method of claim 1 wherein the water-soluble salt is a salt of a mineral or organic acid selected from the group consisting of hydrochloric acid, nitric acid, sulfuric acid, acetic acid, gluconic acid, lactobionic acid, glucoheptonic acid and gluconoglucoheptonic acid.

3. The method of claim 1 wherein the metal is selected from the group consisting of magnesim, calcium, iron, manganese, cobalt and zinc.

4. The method of claim 1 wherein the concentration of the salt of a metal is from 5% by weight of the metallic salt to 25% by weight of the metallic salt.

5. The method of claim 1 wherein the metal salt is a metal gluconate.

6. The method of claim 1 wherein the metal salt is metal lactobionate.

7. The method of claim 1 further containing a pharmacologically-active component which modifies the motility of the digestive tract.

8. The method of claim 1 wherein the contrasting agent is a mixture of 1 to 99% by weight of one metallic derivative selected from the group consisting of the salts and the complexes, the atomic weight of the metal is between 24 and 66 and 99 to 1% by weight of a second metallic derivative defined as above, the atomic weight of the other metal being between 24 and 66.

9. The method of claim 1 wherein the contrasting agent is administered orally or rectally or urogenitally.

* * * * *